(12) United States Patent
Wagers

(10) Patent No.: US 8,285,703 B1
(45) Date of Patent: Oct. 9, 2012

(54) DOCUMENT CRAWLING SYSTEMS AND METHODS

(75) Inventor: Doug R. Wagers, Gardner, KS (US)

(73) Assignee: Softek Solutions, Inc., Prairie Village, KS (US)

( * ) Notice: Subject to any disclaimer, the term of this patent is extended or adjusted under 35 U.S.C. 154(b) by 105 days.

(21) Appl. No.: 12/786,772

(22) Filed: May 25, 2010

Related U.S. Application Data

(63) Continuation of application No. 12/761,454, filed on Apr. 16, 2010, now abandoned.

(60) Provisional application No. 61/177,801, filed on May 13, 2009.

(51) Int. Cl.
 *G06F 7/00* (2006.01)
 *G06F 17/30* (2006.01)
(52) U.S. Cl. .................. 707/709; 707/752
(58) Field of Classification Search ............ 707/709, 707/710, 752, 812
 See application file for complete search history.

(56) References Cited

U.S. PATENT DOCUMENTS

| | | | |
|---|---|---|---|
| 6,263,364 B1 * | 7/2001 | Najork et al. ........... 709/217 |
| 6,351,755 B1 * | 2/2002 | Najork et al. ........... 715/206 |
| 7,185,019 B2 * | 2/2007 | Nayak ................... 707/690 |
| 7,448,022 B1 * | 11/2008 | Ram et al. .............. 717/120 |
| 7,774,782 B1 * | 8/2010 | Popescu et al. ......... 718/104 |
| 7,979,417 B1 * | 7/2011 | Bharat et al. ........... 707/709 |
| 8,180,761 B1 * | 5/2012 | Cooley et al. .......... 707/709 |
| 2006/0149591 A1 * | 7/2006 | Hanf et al. ............. 705/2 |
| 2006/0212350 A1 * | 9/2006 | Ellis et al. ............. 705/14 |
| 2006/0277175 A1 * | 12/2006 | Jiang et al. ............ 707/5 |
| 2008/0147616 A1 * | 6/2008 | Larsson et al. .......... 707/3 |
| 2009/0216747 A1 * | 8/2009 | Li et al. ................. 707/5 |

* cited by examiner

*Primary Examiner* — Merilyn Nguyen
(74) *Attorney, Agent, or Firm* — Polsinelli Shughart PC

(57) ABSTRACT

Systems and methods are provided for crawling and indexing documents stored in a data storage system. A crawler system processes multiple jobs that each correspond to crawling documents in the data storage system. Each job includes priority data and crawling instructions. The crawler system stores each job in a priority queue in a sequence based on the priority data. The crawler system assigns each job in the priority queue to a next available processing module for processing based on the stored sequence. Before processing each job, the crawler system determines whether to segment the job into smaller steps based on the corresponding crawling instructions. If the job is segmented, one of smaller steps is processed to crawl a group of the documents in the data storage system. The remaining steps are stored in the priority queue to wait for processing.

31 Claims, 3 Drawing Sheets

DOCUMENT CRAWLING SYSTEMS AND METHODS

RELATED APPLICATIONS

This application is a continuation of U.S. patent application Ser. No. 12/761,454, filed Apr. 16, 2010, and entitled Document Crawling Systems and Methods, which takes priority to U.S. Patent Application No. 61/177,801, filed May 13, 2009, and entitled Document Crawling Systems and Methods, the entire contents of which are incorporated herein by reference.

FEDERALLY SPONSORED RESEARCH OR DEVELOPMENT

Not Applicable.

COMPACT DISK APPENDIX

Not Applicable.

BACKGROUND

Computer technology has made it possible for business enterprises to store and retrieve enormous quantities of information. For example, healthcare enterprises are increasingly dependent on computer information systems to store and retrieve medical information for patients. Such patient medical information may include text information and image data.

Text information includes, for example, patient identifying information, medical assessment information regarding a patient's medical condition, and/or other textual information that can be recorded about the patient. Image data includes images acquired by various image techniques, such as X-ray imaging, computed tomography X-ray, radioisotope emission imaging, computed emission tomography, magnetic resonance imaging, ultrasonic imaging, and/or any other imaging techniques.

A Picture Archiving and Communication System (PACS) may be used to store, retrieve, and view digital medical images. Separate computer systems may be used to manage text information and image data for a single patient. For example, an administrative computing tool, such as a radiology information system (RIS), can be used by radiology departments to store, manipulate, and distribute patient radiological information, while a PACS system is used to store, retrieve, and view digital medical images.

Due to the volume of information and the need to maintain security, patient medical records are often stored in a separate data storage system, such as a server or other computer system that can store documents. The healthcare enterprise may use a data management system to maintain an indexed database that includes indexed information for patient medical records stored in the data storage system. For example, the data management system may use crawling software (crawler) to search and index medical records from the data storage system for storage in the indexed database system.

Crawlers often require periodic, time consuming, and computationally intensive indexing of all data records being crawled in a data storage system. As a result, the crawling process can be slow, particularly where the number of stored data records being searched is large. Moreover, during the crawling process, other computer systems attempting to access records stored in the data storage system may experience delayed responses or connection errors, such as time-out errors. For example, when crawlers periodically revisit the data storage system to gain updates, the data storage system is required to use its network bandwidth to respond to the crawler. As a result, conventional crawlers can cause the data storage system to expend excess processing time and bandwidth to service crawler requests. Expending processing time and bandwidth in this manner limits the resources available to provide responses to requests received from other computer systems or other applications.

Moreover, the number of documents that can be crawled by a crawler during a selected time-period typically is limited due to network throughput and processing capacity. For example, due to network throughput and processing capacity, the number of documents that can be crawled in an hour in a data storage system storing radiology reports may be limited to 20,000 documents. Crawling all 20,000 documents at one time would require expending significant processing time and adversely impact the performance of the data storage system.

SUMMARY

According to one aspect, a computer-readable medium is encoded with a data management application comprising modules executable by a processor to crawl a plurality of documents. The data management application includes a scheduling module to retrieve a plurality of job modules from a data store. The plurality of job modules each include corresponding crawling instructions and priority data for crawling documents in a data storage system. The data management application also includes a priority queue to receive the plurality of job modules from the scheduling module and to store each job module in a sequence according to the priority data. The data management application also includes an execution module to assign each job module to one of a plurality of processing modules according to the sequence for processing. Each assigned job module is configured to identify a step for processing based on the corresponding crawling instructions. The step includes crawling a group of the documents. The assigned job module is configured to process the step to crawl the group of the documents in the data storage system. Each assigned job module is also configured to determine if at least one additional step for processing is required based on the corresponding crawling instructions. The at least one additional step includes crawling another group of the documents. Each assigned job module is also configured to reschedule the assigned job module to the scheduling module for insertion into the priority queue.

According to another aspect, a system for crawling documents includes a data store to store a plurality of job modules. Each of the plurality of jobs modules includes corresponding crawling instructions and priority data for crawling documents in a data storage system. The system also includes a processing device comprising a data management application comprising modules executable by the processing device to crawl the documents. The data management application includes a scheduling module to retrieve the plurality of job modules from the data store. The data management application also includes a priority queue to receive the plurality of job modules from the scheduling module and to store each job module in a sequence according to the corresponding priority data. The data management application also includes an execution module to assign each job to one of a plurality of processing modules according to the sequence for processing. Each assigned job module is configured to identify a step for processing based on the corresponding crawling instructions. The step includes crawling a group of the documents. The assigned job module is configured to process the step to crawl the group of the documents in the data storage system.

Each assigned job module is also configured to determine if at least one additional step for processing is required based on the corresponding crawling instructions. The at least one additional step includes crawling another group of the documents. Each assigned job module is also configured to reschedule the assigned job module to the scheduling module for insertion into the priority queue.

According to another aspect, a method for crawling documents includes executing a data management application on a processing device to crawl the documents in a data storage system. The data management application includes a scheduling module, a priority queue, a plurality of processing modules, and an execution module. The method also includes retrieving a plurality of job modules from a data store at the scheduling module. The plurality of job modules each include corresponding crawling instructions and corresponding priority data for crawling documents in a data storage system. The method also includes transferring the plurality of job modules from the scheduling module to the priority queue. The method also includes storing each job module in a sequence in the priority queue according to the priority data. The method also includes assigning, at the execution module, each job module to one of a plurality of processing modules according to the sequence for processing. The method also includes identifying a step for processing at an assigned processing module based on the corresponding crawling instructions. The step includes crawling a group of the documents. The method also includes processing the step to crawl the group of the documents in the data storage system. The method also includes determining if at least one additional step for processing is required based on the corresponding crawling instructions. The at least one additional step includes crawling another group of the documents. The method also includes rescheduling the assigned job module to the scheduling module for insertion into the priority queue.

According to one aspect, a computer-readable medium is encoded with a data management application comprising modules executable by a processor to crawl a plurality of documents. The data management application includes a scheduling module to retrieve a plurality of job modules from a data store. The plurality of job modules each include corresponding crawling instructions, status data, and priority data for crawling documents in a data storage system. The data management application also includes a priority queue to receive the plurality of job modules from the scheduling module and to store each job module in a sequence according to the priority data. The data management application also includes an execution module to assign each job module to one of a plurality of processing modules according to the sequence for processing. Each assigned job module is configured to identify a step for processing based on the corresponding crawling instructions and status data. The step includes crawling a group of the documents. The status data indicates whether the step has been processed. The assigned job module is configured to process the step to crawl the group of the documents in the data storage system. Each assigned job module is also configured to determine if at least one additional step for processing is required based on the corresponding crawling instructions. The at least one additional step includes crawling another group of the documents. Each assigned job module is also configured to reschedule the assigned job module to the scheduling module for insertion into the priority queue.

DETAILED DESCRIPTION

Figure 1:
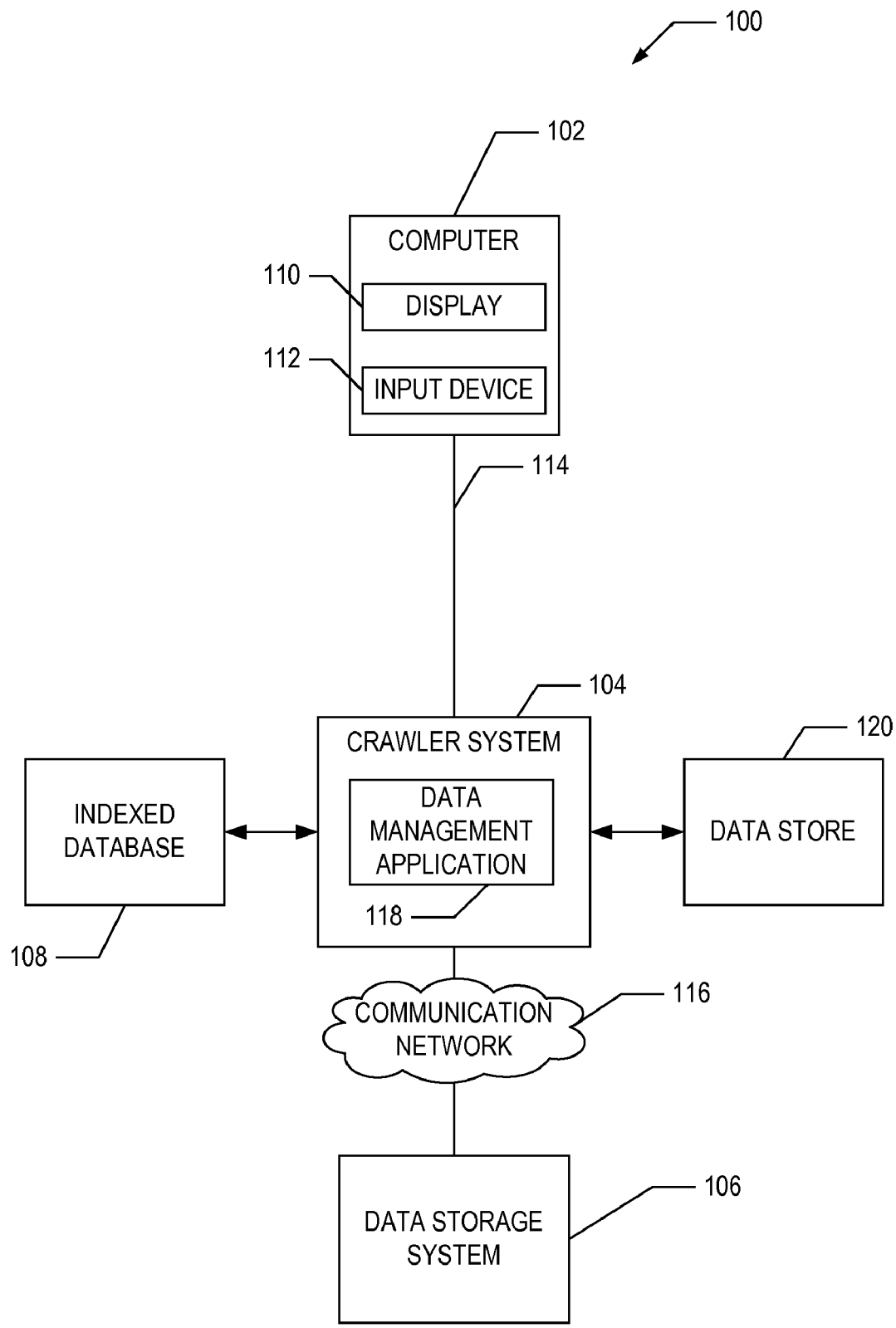
FIG. 1 is a block diagram of a computing environment for implementing a data management system according to one aspect of the invention.

The process of crawling and indexing documents can be separated into a number of distinct jobs with differing scheduled intervals for processing. A job module or job includes code or instructions that specify a unit of work and how the unit of work is to be processed or be performed by a processing system, such as a computer. A job also includes information about itself, such as a priority level for processing the job and which, if any steps of a job have been processed. In one aspect, a job includes the process of crawling and indexing documents. For example, one job detects changes to documents. In another aspect, a job includes a search or query of data.

Aspects of the crawler system described herein enable the crawling and indexing of documents and/or data stored in a data storage system. The data storage system is, for example, a server or other computing system that is accessible by one or more computer systems. A crawler system employs a data management application that crawls documents and/or data stored in the data storage system with negligible impact on the performance of the data storage system as perceived by the one or more computer systems. For example, the data management application enables a particular computer system to crawl documents and/or data stored in the data storage system in such a manner that minimizes delayed responses and/or connection errors experienced by one or more other computer systems attempting to access the data storage system.

In one aspect of the crawler system, multiple jobs are used. To minimize the impact to the system being crawled, the total number of simultaneously executing jobs is limited in one embodiment. In one example, the system has two jobs executing at the same time.

In another aspect of the crawler system, all jobs are not processed at the same time. Multiple jobs with differing scheduled intervals are executed. In one example, documents with differing age ranges are crawled as different jobs. In another example, documents created or edited more recently are crawled more often than older documents edited or created less recently.

Job starvation occurs when a particular job is unable to be processed because one or more other jobs are currently being processed and are not yielding sufficient processing capacity or resources required to process that particular job. For example, a job that crawls and indexes documents created in the last twenty-four (24) hours could be starved by a larger job that crawls and indexes documents older than ninety (90) days where more processing resources are required to crawl the older documents.

Aspects of the crawler system prevent job starvation during a crawling process. As explained in more detail below, the data management application prevents starvation by segmenting larger jobs into smaller steps based on instructions included in the job. The data management application then schedules a time for performing smaller jobs and each step of a segmented large job. After performing a smaller step of the larger job, the data management application schedules a new time for executing the unperformed steps of that particular job. By separating larger jobs into a plurality of steps and performing only one step of the job at a time, other jobs, such as smaller jobs originating from other computer systems or other crawling jobs, can be performed without waiting for the larger job to be completed.

The crawler system crawls, indexes, searches, and returns results of searches for one or more records, documents, and other data, such as radiological examination documents and data, electronic health records (EHRs), electronic medical records (EMRs), patient records and documents, other medical or healthcare records, documents, and data, images and image documents, imaging data generated via a PACS system or other imaging system, and/or other data. The data includes structured and unstructured (free text) data. Structured data is data in or associated with defined fields, such as a name, a data of birth, or a medical record number (MRN). Unstructured data is free text not in or associated with a defined field. An example of unstructured data includes examination (exam) notes from a medical practitioner. The system also crawls, indexes, searches, and returns results of searches for hypertext markup language (HTML) pages and other web pages in one embodiment.

Data also includes images associated with unstructured data and/or structured data or tags. A tag is one or more words, symbols, or other characters assigned to an image or a text document. The tag can describe an image document or a text document or indicate information about image or text documents. The crawler system can crawl image and text documents stored in the data storage system based on assigned tags.

FIG. 1 is a block diagram of an exemplary computing environment 100 for managing the crawling of documents according to an aspect of the present invention. The computing environment 100 includes at least one computer 102, a crawler system 104, a data storage system 106, and an indexed database system (indexed database) 108.

According to one aspect, the computer 102 is a computing or processing device, such as a personal computer, a server computer, or a mobile processing device. The computer 102 includes one or more processors that process software or other machine-readable instructions and memory to store the software or other machine-readable instructions and data. The memory may include volatile and/or non-volatile memory. The computer 102 also includes a communication system to communicate via wireline and/or wireless communications, such as through the Internet, an intranet, an Ethernet network, a wireline network, a wireless network, and/or another communication network. The computer 102 may include a display 110 for viewing data, such as a computer monitor, and an input device 112, such as a keyboard or a pointing device (e.g., a mouse, trackball, pen, touch pad, or other device), for entering data and navigating through data, including exams, images, documents, structured data, unstructured data, HTML pages, other web pages, and other data.

The computer 102 can be used by a user to request data from the data source 106, including healthcare data and medical data, records, documents, and/or images. In one example, the input device 112 is used to interact with data and/or fields displayed on a user interface screen (not shown). Although one computer 102 is depicted in FIG. 1, the computing environment 100 may include multiple computers.

In one example, the computer 102 is used by a business enterprise, such as a healthcare enterprise, to enable a user to request documents and data from an indexed database 108 or the data storage system 106. According to one aspect, users use the computer 102 to generate a search request 114 to search for one or more records, documents, and other data, such as radiological examination documents and data, EHRs, EMRs, patient records and documents, other medical or healthcare records, documents, and data, images and image documents, imaging data generated via a PACS system or other imaging system, HTML pages, other web pages, and/or other data. The generated search request 114 includes a textual string that includes one or more search terms. The computer 102 transfers the search request 114 to the crawling system 104. The computer 102 may be used by other enterprises, such as an educational institution, a government institution, and other environments. Other examples exist.

According to one aspect, users use the computer 102 to generate a search request 114, to search medical records of a patient. For example, the user uses the keyboard to interact with a search entry screen of a user interface on the display 110 to enter a search that includes one or more search terms. After entering the search terms, the user uses the input device 112 to select an input control, such as a search control button, displayed on the entry screen to generate the search request 114.

The crawling system 104 submits a corresponding query to the indexed database 108 to retrieve results in response to the search request 114. For example, the crawling system 104 queries the indexed database 108 to retrieve one or more medical records that match the one or more search terms included in the search request 114. Each medical record may include structured data, unstructured data, one or more images, and/or other data.

The crawling system 104 also periodically crawls documents in the data storage system 106 and indexes document data for storage in the indexed database 108. Document data may include document content and document metadata. Document content includes images and/or text, including structured data and/or unstructured data. Document data may include a copy of all content or a portion of the content for a particular document. Metadata includes document creation and edit dates, a storage location on a network or the data storage system 106, creating and editing users, and other information about the document and/or the data storage system 106.

According to one aspect, the crawling system 104 communicates with the data storage system 106 over a communication network 116 using a communication protocol. The communication network 116 can be the Internet, an intranet, an Ethernet network, another wireline network, a wireless network, and/or another communication network. According to another aspect, the crawling system 104 may be connected directly to the data storage system 106. In another aspect, the computer 102 communicates with the crawler system 104 through the communication network 116. In still another aspect, one or more of the indexed database 108 and/or the data store 120 communicate with the crawler system through the communication network 116.

The crawling system 104 executes a data management application 118 to manage the sequence and timing at which documents in the data storage system 106 are crawled and document data is indexed for storage in the indexed database 108. The data management application 118 is, for example, a crawling application that searches documents in the data storage system 106 and indexes document data for storage in the indexed database 108 in a searchable form. As explained in more detail below, the data management application 118 uses data stored in a data store 120 to determine a sequence for crawling documents in the data storage system 106. The data store 120 stores a general repository of data, such as scheduling data, priority data, and/or instructions related to the crawling and/or retrieval of documents. As used herein, crawling includes searching and indexing documents stored in a data source. The data storage system 106 is one example of a data source.

The data storage system 106, the indexed database 108, and the data store 120 may include memory and one or more processors or processing systems to receive, process, and transmit communications and store and retrieve data.

In one embodiment, the data management application 104 is integrated with a PACS. In another embodiment, the data management application 104 is integrated with a data storage system 106 having PACS documents and other PACS records, including radiology exams and radiology images.

Figure 2A:
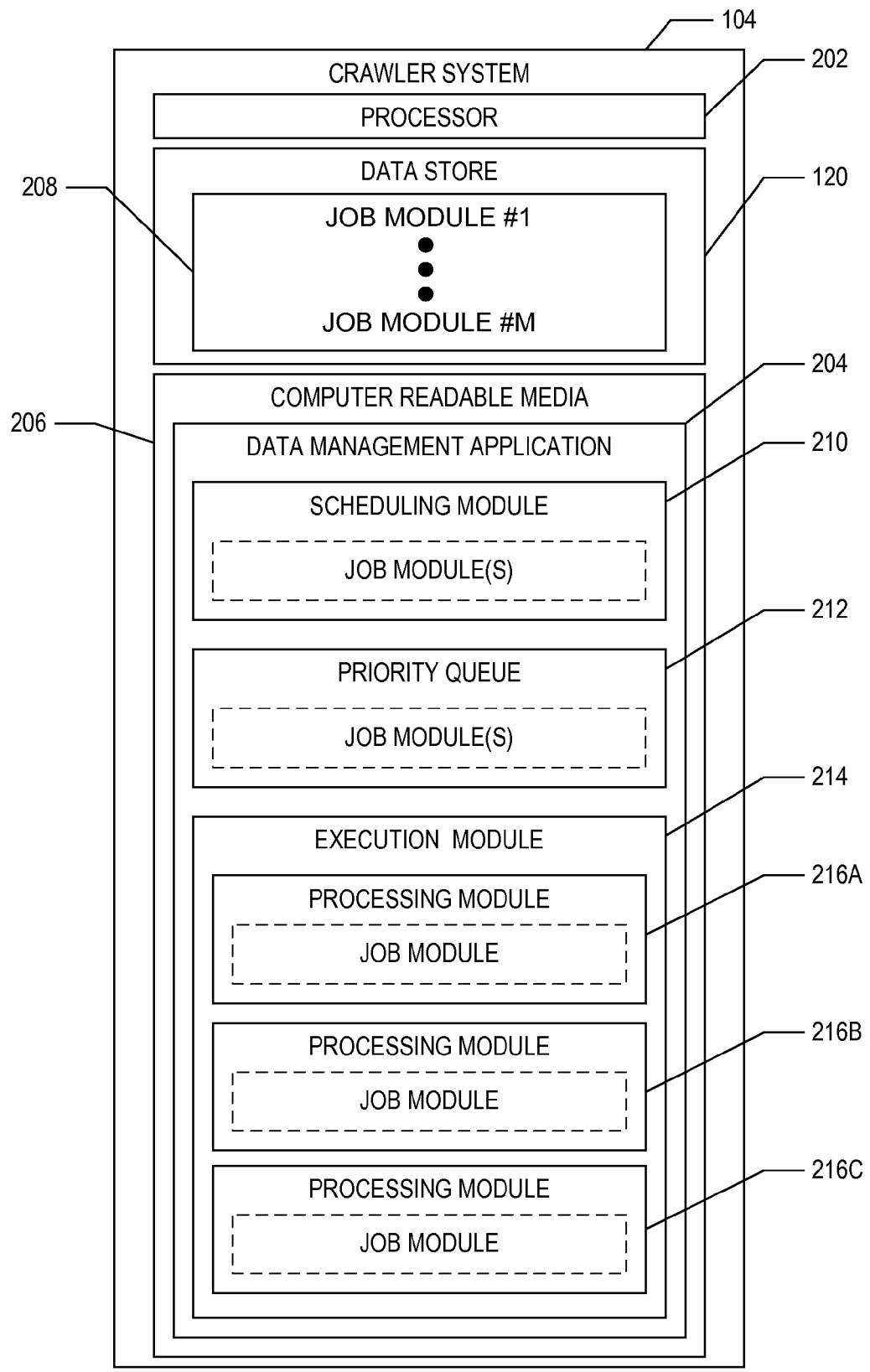
FIG. 2A is a block diagram of a data management application according to one aspect of a data management system.

FIG. 2A is a block diagram that depicts an exemplary crawling system 104. According to one aspect, the crawling system 104 includes a processing system 202 that executes a data management application (DMA) 204 to manage the sequence and timing at which documents in the data storage system 106 are crawled.

The DMA 204 includes instructions or modules that are executable by the processing system 202 of the crawling system 104 to manage the crawling and/or retrieval of documents from the data storage system 106. The crawling system 104 includes a computer readable media 206 configured with the DMA 204.

The computer readable media (CRM) 206 may include volatile media, nonvolatile media, removable media, non-removable media and/or another available medium that can be accessed by the crawling system 104. By way of example and not limitation, computer readable media 206 comprises computer storage media and communication media. Computer storage media includes memory, volatile media, nonvolatile media, removable media, and/or non-removable media implemented in a method or technology for storage of information, such as computer readable instructions, data structures, program modules, or other data. Communication media may embody computer readable instructions, data structures, program modules, or other data and include an information delivery media or system.

Figure 2B:
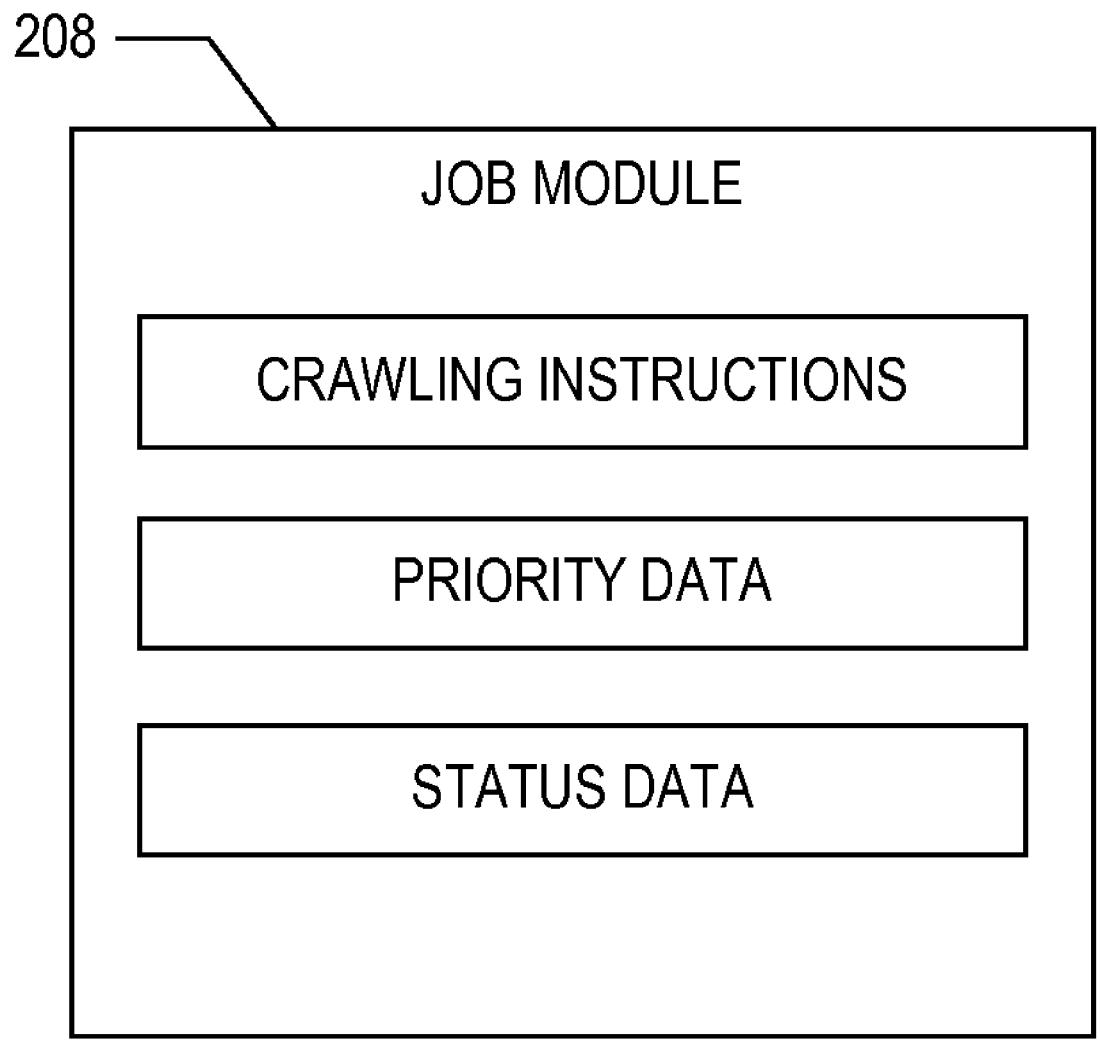
FIG. 2B depicts data and instruction components of a job module according to one aspect of a data management system.

The data store 120 is, for example, a computer storage media that stores one or more job modules 208. The data store 120 may store one job module 208 or a number (e.g., #M) of job modules 208. Each job module 208 includes code or instructions that specify a unit of work and how the unit of work is to be processed or be performed by the processing system 202. Each job module 208 also includes priority data for determining a priority for processing the job module 208. For example, one job module 208 may include priority data and instructions for crawling documents in the data storage system 106 that were created, edited, and/or stored within a first selected period or range of time. As another example, another particular 208 module may include different priority data and different instructions for crawling documents that were created, edited, and/or stored within a second selected time-period, including a time-period that is in chronological sequence with the first time-period. FIG. 2B depicts data and instruction components of a job module 208.

Other job modules 208 may include crawling instructions for crawling documents based on the type of system that created the document (e.g., radiology or PACS systems), the type of department associated with the document, or the practice area of a medical practitioner that created the document.

According to one aspect, the priority data and/or crawling instructions for a corresponding job module 208 is predefined. For example, a system administrator may use an administrative computing device (not shown) to define the priority data and crawling instructions for a particular job module 208 for storage in the data store 120. Although the data store 120 is depicted in FIG. 2A as being integrated within the crawling system 204, it is contemplated the data store 120 may be external to the crawling system 104, such as depicted in FIG. 1.

Upon execution of the DMA 204, a scheduling module 210 retrieves job modules 208 from the data store 120. The scheduling module 210 then sends the job modules 208 to a priority queue 212 to wait for processing.

The priority queue 212 stores job modules 208 in a sequence based on their corresponding priority data. For example, the priority queue 212 stores each of the job modules 208 in a descending order based on a priority level defined by corresponding priority data included in each job module 208. The priority level is, for example, a rating, or value associated with each job module 208 that defines an order or sequence for processing that job module 208.

Priority data may include predefined data that indicates a priority for executing one job module 208 relative to another job module 208 based on the document type. For example, job modules 208 associated with crawling computed tomography (CT) image documents might have a higher priority level than non-CT image documents. As a result, in this example, job modules that involve crawling CT image documents have a higher priority than non-CT image documents. Priority data may also include predefined data that indicates a priority for executing one job module 208 relative to another job module 208 based on the date the document was created or edited. For example, job modules 208 associated with crawling documents that were created or edited within the last twenty-four (24) hours may have a higher priority level than job modules 208 associated with crawling documents that were created or edited 30 days ago.

According to one aspect, the priority level depends on a size of the job module 208. The size of the job module 208 can refer to the number of documents to be crawled and/or the time-period during which the documents to be crawled were created or edited. For example, a large job module 208 may correspond to crawling all documents older than ninety (90) days. A small job module 208 may correspond to crawling documents that were created or edited within the past twenty-four (24) hours.

According to another aspect, the crawling instructions for a particular job module 208 may specify a plurality of steps for processing that particular job module 208. For example, the particular job module 208 may involve searching a large number of documents. Due to the large number of documents, the crawling instructions segments job module 208 into smaller steps. As an example, the particular job module 208 may involve crawling documents that were created or updated within a selected time-period, such as documents created in the last thirty-six (36) hours. In this example, the crawling instructions may segment the particular job module 208 into a first step and second step. The first step may involve crawling documents updated or added to the data storage system between eighteen (18) to thirty-six (36) hours from a present time. The second step may involve crawling documents updated or added to the data storage system 106 between zero (0) to eighteen (18) hours from the present time. Although the crawling instructions are described as segmenting the particular job module 208 into a first step and second step, it is contemplated that the crawling instructions may be configured to segment a particular job module 208 into two or more steps.

According to another aspect, the priority level of a particular job module 208 is determined based on status data associated with that particular job module 208. The status data associated with a particular job module 208 indicates whether one or more steps of that particular job module 208 have been performed. For example, if a job module #1 and a job module #2 have the same priority data, the status data for each of these two job modules can specify which has priority. In this example, if job module #1 includes status data that indicates at least one step of job module #1 has been processed and job module #2 includes status data that indicates no steps of job module #2 have been performed, the priority level associated with job module #1 is higher than job module #2.

According to another aspect, the crawling instructions for each job module 208 defines a recurrence interval that specifies when the next step of a job module 208 can be processed. For example, the recurrence interval specifies a time interval that must expire before another step of a job module 208 can be executed. According to one aspect, the recurrence interval is offset from the completion time of the previous step rather than the start time of the previous step. As a result, smaller jobs that run frequently and take longer to execute than their recurrence interval are prevented from being immediately rescheduled.

According to another aspect, the recurrence interval specifies when a step of a job module 208 can be reprocessed. For example, if a job module 208 only includes one step, the recurrence interval defined by crawling instructions specifies a time interval the must expire prior to reprocessing the job module 208.

An execution module 214 retrieves job modules 208 from the priority queue 212 for assignment to one of multiple processing modules 216A, 216B, and 216C for processing. For example, the job module 208 with the highest priority level value in the priority queue 212 will be assigned to the next available one of the processing modules. In one example, the processing modules become available for processing job modules 208 in the following order: processing module 216A, processing module 216B, and processing module 216C. In this example, the execution module 214 assigns the job module 208 with the highest priority level value in the priority queue 212 to processing module 216A to be processed first. The execution module 214 then assigns the job module 208 with the next highest priority level value in the priority queue 212 to processing module 216B to be processed. This process repeats for each job module 208 in the priority queue 212 such that the order in which job modules 208 are assigned to available processing modules corresponds to their priority levels.

According to another aspect, the execution module 214 assigns job modules to processing modules based on their sequence in the priority queue 212. For example, job modules 208 that have the same priority data are stored in the priority queue 212 based on first-in first-out (FIFO) rules. Accordingly, the execution module 214 assigns such job modules 208 to the processing modules 216A, 216B, and 216C based on FIFO rules.

After performing one step of a particular job module 208, the processing module 216A sends the unperformed steps of that particular job module 208 back to the scheduling module 210. The scheduling module 210 then sends the unperformed steps of that particular job module 208 to the priority queue 212 to wait for assignment to the processing modules 216A, 216B, and 216C. By separating or segmenting job modules into a plurality of steps and performing only one step of the job module at a time, other jobs, such as smaller jobs, can be performed without waiting for the entire assigned job to be completed.

Those skilled in the art will appreciate that variations from the specific embodiments disclosed above are contemplated by the invention. The invention should not be restricted to the above embodiments, but should be measured by the following claims.

What is claimed is:

1. A non-transitory computer-readable medium encoded with a data management application comprising modules executable by a processor to crawl documents, the data management application comprising:
   a scheduling module to retrieve a plurality of job modules from a data store, the plurality of job modules each comprising corresponding crawling instructions and corresponding priority data for crawling documents in a data storage system;
   a priority queue to receive the plurality of job modules from the scheduling module and to store each job module in a sequence according to the corresponding priority data;
   an execution module to assign each job module to one of a plurality of processing modules according to the sequence for processing, wherein each assigned job module is configured to:
      identify a step for processing based on the corresponding crawling instructions, the step comprising crawling a group of the documents;
      process the step to crawl the group of the documents in the data storage system;
      determine if at least one additional step for processing is required based on the corresponding crawling instructions, the at least one additional step comprising crawling another group of the documents; and
      reschedule the job module to the scheduling module for insertion into the priority queue.

2. The computer-readable medium of claim 1 wherein the corresponding priority data identifies a priority for processing each of the plurality of job modules based on a type of the documents being crawled or based on a time the documents being crawled were created or edited.

3. The computer-readable medium of claim 1 wherein the documents comprise healthcare documents.

4. The computer-readable medium of claim 1 wherein the documents comprise at least one member of a group consisting of radiological examination documents, electronic health records (EHRs), electronic medical records (EMRs), patient records, patient documents, image documents, and imaging data in a Picture Archiving and Communication System (PACS).

5. The computer-readable medium of claim 1 wherein the documents further comprise structured data and unstructured data.

6. The computer-readable medium of claim 1 wherein the corresponding crawling instructions of the assigned job module identify documents to crawl in the data storage system based on a date range, wherein the step comprises crawling documents within a portion of the date range, and wherein the at least one additional step comprises crawling documents within a remaining portion of the date range.

7. The computer-readable medium of claim 6 wherein:
   the corresponding crawling instructions of the assigned job module identify a time interval; and
   the execution module is further configured to assign the rescheduled job module to one of the plurality of processing modules to process the at least one additional step to one of the plurality of processing modules after expiration of the time interval when the at least one additional step is required.

8. The computer-readable medium of claim 7 wherein the execution module assigns the rescheduled job module to one of the plurality of processing modules to reprocess the step after expiration of the time interval when the at least one additional step is not required.

9. The computer-readable medium of claim 1 wherein each of plurality of job modules further comprises status data indicating whether the step or the at least one additional step has been processed.

10. The computer-readable medium of claim 9 wherein each assigned job module is further configured to identify the step or the at least one additional step for processing based on the crawling instructions and the status data.

11. The computer-readable medium of claim 1 wherein the priority data for each job module comprises a corresponding predefined priority level, wherein the priority queue stores each job module in the sequence according to the corresponding predefined priority level.

12. A system for crawling documents, the system comprising:
 a data store to store a plurality of job modules, each of the plurality of jobs job modules comprising corresponding crawling instructions and corresponding priority data for crawling documents in a data storage system;
 a processing device comprising a data management application comprising modules executable by the processing device to crawl the documents, the data management application comprising:
  a scheduling module to retrieve the plurality of job modules from the data store; and
  a priority queue to receive the plurality of job modules from the scheduling module and to store each job module in a sequence according to the corresponding priority data; and
 an execution module to assign each job module to one of a plurality of processing modules according to the sequence for processing, wherein each assigned job module is configured to:
  identify a step for processing based on the corresponding crawling instructions, the step comprising crawling a group of the documents;
  enable the processing module to process the step to crawl the group of the documents in the data storage system;
  determine if at least one additional step for processing is required based on the corresponding crawling instructions, the at least one additional step comprising crawling another group of the documents; and
  reschedule the job module to the scheduling module for insertion into the priority queue.

13. The system of claim 12 wherein the corresponding priority data identifies a priority for processing each of the plurality of job modules based on a type of the documents being crawled or based on a time the documents being crawled were created or edited.

14. The system of claim 12 wherein the documents comprise at least one member of a group consisting of radiological examination documents, healthcare documents, electronic health records (EHRs), electronic medical records (EMRs), patient records, patient documents, image documents, and imaging data in a Picture Archiving and Communication System (PACS).

15. The system of claim 12 wherein the documents comprise structured data and unstructured data.

16. The system of claim 12 wherein the corresponding crawling instructions of the assigned job module identify documents to crawl in the data storage system based on a date range, wherein the step comprises crawling documents within a portion of the date range, and wherein the at least one additional step comprises crawling documents within another portion of the date range.

17. The system of claim 16 wherein:
 the corresponding crawling instructions of the assigned job module identify a time interval; and
 the execution module is further configured to assign the rescheduled job module to one of the plurality of processing modules to process the at least one additional step to one of the plurality of processing modules after expiration of the time interval when the at least one additional step is required.

18. The system of claim 17 wherein the execution module assigns the rescheduled job module to one of the plurality of processing modules to reprocess the step after expiration of the time interval when the at least one additional step is not required.

19. The system of claim 12 wherein each of plurality of job modules further comprises status data indicating whether the step or the at least one additional step has been processed.

20. The system of claim 19 wherein each assigned job module is further configured to identify the step for processing based on the crawling instructions and the status data.

21. The system of claim 12 wherein the priority data for each job module comprises a corresponding predefined priority level, wherein the priority queue stores each job module in the sequence according to the corresponding predefined priority level.

22. A method for crawling documents, the method comprising:
 executing a data management application on a processing device to crawl documents in a data storage system, the data management application comprising a scheduling module, a priority queue, a plurality of processing modules, and an execution module;
 retrieving a plurality of job modules from a data store at the scheduling module, the plurality of job modules each comprising corresponding crawling instructions and corresponding priority data for crawling documents;
 transferring the plurality of job modules from the scheduling module and to the priority queue;
 storing each job module in a sequence in the priority queue according to the corresponding priority data;
 assigning, at the execution module, each job module to one of a plurality of processing modules according to the sequence for processing;
 identifying a step for processing at an assigned processing module based on the corresponding crawling instructions, the step comprising crawling a group of the documents;
 processing the step at the assigned processing module to crawl the group of the documents in the data storage system;
 determining if at least one additional step for processing is required based on the corresponding crawling instructions, the at least one additional step comprising crawling another group of the documents; and
 rescheduling the assigned job module to the scheduling module for insertion into the priority queue.

23. The method of claim 22 wherein the priority data identifies a priority for processing each of the plurality of job modules based on a type of the documents being crawled or based on a time the documents being crawled were created or edited.

24. The method of claim 22 wherein the documents comprise at least one member of a group consisting of radiological examination documents, healthcare documents, electronic health records (EHRs), electronic medical records (EMRs), patient records, patient documents, image documents, and imaging data in a Picture Archiving and Communication System (PACS).

25. The method of claim 22 wherein the documents comprise structured data and unstructured data.

26. The method of claim 22 wherein the corresponding crawling instructions of the assigned job module identify documents to crawl in the data storage system based on a date range, wherein the first step comprises crawling documents within a portion of the date range, and wherein the at least one additional step comprises crawling documents within a remaining portion of the date range.

27. The method of claim 26 wherein:
the corresponding crawling instructions of the assigned job module identify a time interval; and
the method further comprising assigning, at the execution module, the at least one additional step to one of the plurality of processing modules after expiration of the time interval when the at least one additional step is required.

28. The method of claim 27 further comprising assigning, at the execution module, the rescheduled job module to one of the plurality of processing modules to reprocess the step after expiration of the time interval when the at least one additional step is not required.

29. The method of claim 22 wherein each of plurality of job modules further comprises status data indicating whether the step or the at least one additional step has been processed.

30. The method of claim 29 further comprising to identifying the step for processing job module based on the crawling instructions and the status data.

31. A non-transitory computer-readable medium encoded with a data management application comprising modules executable by a processor to crawl documents, the data management application comprising:
a scheduling module to retrieve a plurality of job modules from a data store, the plurality of job modules each comprising corresponding crawling instructions, corresponding status data, and corresponding priority data for crawling documents in a data storage system;
a priority queue to receive the plurality of job modules from the scheduling module and to store each job module in a sequence according to the corresponding priority data; and
an execution module to assign each job module to one of a plurality of processing modules according to the sequence for processing, wherein each assigned job module is configured to:
identify a step for processing based on the corresponding crawling instructions and the corresponding status data, the step comprising crawling a group of the documents, and the status data indicating whether the step has been processed;
process the step to crawl the group of the documents in the data storage system;
determine if the at least one additional step for processing is required based on the corresponding crawling instructions, the at least one additional step comprising crawling another group of the documents; and
reschedule the assigned job module to the scheduling module for insertion into the priority queue.

* * * * *